United States Patent [19] [11] 4,404,282
Nakatsukasa [45] Sep. 13, 1983

[54] PROCESS FOR ENZYME INHIBITOR

[75] Inventor: Walter M. Nakatsukasa, Indianapolis, Ind.

[73] Assignee: Eli Lilly and Company, Indianapolis, Ind.

[21] Appl. No.: 409,764

[22] Filed: Aug. 19, 1982

[51] Int. Cl.³ .................. C12P 17/12; C12P 17/10; C12R 1/465

[52] U.S. Cl. ............................ 435/122; 435/121; 435/886

[58] Field of Search ................. 435/122, 121, 169

[56] References Cited

U.S. PATENT DOCUMENTS

| | | | |
|---|---|---|---|
| 4,046,889 | 9/1977 | Ondetti et al. | 424/244 |
| 4,154,935 | 5/1979 | Ondetti et al. | 546/189 |
| 4,226,879 | 10/1980 | Omura et al. | 435/169 X |
| 4,316,905 | 2/1982 | Krapcho | 424/274 |
| 4,316,906 | 2/1982 | Ondetti et al. | 424/274 |

OTHER PUBLICATIONS

Cushman, D. W. et al., Federation Proceedings, vol. 38, No. 13, Dec. 1979.
Derwent abstract 25836D/15 of EP25-941.
A. A. Patchett et al., Nature, 288:280-283, 1980.

Primary Examiner—Lionel M. Shapiro
Attorney, Agent, or Firm—William B. Scanlon; Arthur R. Whale

[57] ABSTRACT

Angiotensin I converting enzyme inhibitor A-58365 factor B is provided in greater abundance than coproduced Factor A by culturing *Streptomyces chromofuscus* NRRL 15098 under submerged aerobic fermentation conditions in an aqueous nutrient culture medium supplement with the amino acids proline and lysine.

4 Claims, No Drawings

PROCESS FOR ENZYME INHIBITOR

BACKGROUND OF THE INVENTION

This invention relates to an improved fermentation process for producing angiotensin I converting enzyme inhibitor A-58365 factor B. In particular, it relates to an improved fermentation process for producing A-58365 factor B which comprises culturing *Streptomyces chromofuscus* NRRL 15098 under submerged aerobic fermentation conditions in an aqueous nutrient culture medium supplemented with the amino acids proline and lysine.

The angiotensin I converting enzyme inhibitors A-58365 factors A, B, and C and the process for the production thereof are described in copending application Ser. No. 409,763 filed this even date (attorney docket No. X-5950). A-58365 factor A is the major factor, i.e. most abundant, produced in the fermentation of *S. chromofuscus* NRRL 15098, while factors B and C are produced in minor amounts in relation to factor A. In copending application Ser. No. 409,765 filed this even date there is described an improved process for producing A-58365 factor A in greater abundance which comprises culturing the *S. chromofuscus* strain in an aqueous nutrient culture medium containing between about 1 g and about 6 g of proline per liter of culture medium. According to the process of the present invention, when between about 1 g and about 3 g of lysine is added to the proline containing culture medium for *S. chromofuscus* the fermentation provides surprisingly enhanced yields of A-58365 factor B with factor B now being produced in greater abundance than factor A.

DESCRIPTION OF THE PRIOR ART

The decapeptide angiotensin I, previously referred to as hypertensin and angiotonin, is converted by ACE to the octapeptide angiotensin II. The converting enzyme ACE splits off the C-terminal histadyl leucyl residue of angiotensin I to form angiotensin II. Angiotensin II is a potent vasoconstrictor and acts directly on the adrenal gland to stimulate the release of aldosterone, M. Bodanszky, M. A. Ondetti, *Peptide Synthesis*, John Wiley, New York, 1966, pp. 215-223, and Pumpus, "Angiotensin", *Renal Hypertension*, I. Page, J. McCubbin, eds. (Yearbook Medical Publishers, Chicago, IL,. 1968), pp. 62-68. Angiotensin I is formed by the action of the enzyme renin on the substrate, angiotensinogen. The role of the renin-angiotensin system in the etiology of hypertension has been much studied. See, for example, *J. Med. Chem.*, 24 (4), 355-361 (1981) and references cited therein.

Synthetic compounds which inhibit the action of ACE and which have hypotensive properties have been described previously, for example, the mercaptoacyl derivatives of substituted prolines disclosed in U.S. Pat. No. 4,316,904, Feb. 23, 1982, and U.S. Pat. No. 4,316,906, Feb. 23, 1982; the mercapto-substituted derivatives of certain amino acids disclosed in U.S. Pat. No. 4,154,936, May 15, 1979; the hydroxycarbamoyl derivatives of pipecolic acid disclosed in U.S. Pat. No. 4,154,937, May 15, 1979; and the mercaptoacyl derivatives of certain azetidine-2-carboxylic acids disclosed by U.S. Pat. No. 4,046,889, Sept. 6, 1977.

DETAILED DESCRIPTION

The process for producing A-58365 factor B provided by this invention comprises culturing the new strain of *Streptomyces chromofuscus* NRRL 15098 in an aqueous nutrient culture medium under submerged aerobic fermentation conditions, wherein the culture medium is supplemented with between about 1 g and about 6 g of proline per liter and with between about 1 g and 3 g of lysine per liter. The fermentation is carried out under substantially the same conditions of aeration, pH, and time of fermentation as described in copending application Ser. No. 409,765. The nutrient culture medium employed contains the same sources of carbon, nitrogen and inorganic salts as described hereinafter and, in addition, the amino acids proline and lysine.

The fermentation can be carried out at a temperature between about 25° C. and about 35° C. The fermentations carried out at about 30° C. afford the highest assays for factor B and, accordingly, about 30° C. is the preferred temperature.

The amino acids proline and lysine can be used in the L-form, the D-form or in the D,L-form. Other sources of the amino acids such as protein hydrolysates and enzymatic digests containing proline and lysine can be added to the culture medium to supply the amino acids. Because of their lower costs, L-proline and L-lysine are the preferred forms of the amino acids. Both of the amino acids, proline and lysine, are required constituents of the culture medium for the enhanced production of factor B. The fermentation carried out with only incorporated proline provides surprisingly higher yields of A-58365 factor A (copending application Ser. No. 409,765) while fermentations carried out only with a lysine supplemented culture medium do not have any appreciable effect on the yields of either factor.

Preferably, between about 3 g and about 4 g of proline and about 2 g of lysine per liter of culture medium are employed in the process.

Prior to the discovery of the improved process of this invention, the proline supplemented *S. chromofuscus* NRRL 15098 culture medium provided on fermentation about 11 mcg/ml of factor A and about 2-3 mcg/ml of the minor factor B. A-58365 factor C occurs in even lesser amounts than factor B. When *S. chromofuscus* NRRL 15098 is cultured according to the process of this invention assays show that about 5 mcg/ml of factor B are produced while between about <1 mcg/ml and about 2 mcg/ml of factor A are produced.

Accordingly, this invention provides a process for obtaining as the most abundant angiotensin converting enzyme inhibitor, A-58365 factor B.

Factor B is recovered from the filtered fermentation broth and separated from factor A and purified by following the isolation procedures described by copending application Ser. No. .

The characterization of the A-58365 factors, the fermentation method by which they are produced, the new strain of *S. chromofuscus* NRRL 15098, and the recovery and isolation of the factors are described in copending application Ser. No. 409,765 and hereinafter.

A-58365 Factor A

Factor A is isolated, as described hereinafter, as a white amorphous powder and is highly soluble in water and polar organic solvents such as methyl alcohol, ethyl alcohol, dimethylformamide and dimethylsulfoxide. It is sparingly soluble in acetone and is insoluble in hydrocarbon solvents such as benzene and hexane.

Factor A absorbs radiation in the ultraviolet region of the spectrum. The following ultraviolet absorption spectrum of factor A was run on a Varian Cary spectrophotometer model 118. The spectrum was obtained on an aqueous solution of factor A under neutral, acidic, and alkaline conditions.

Neutral and acidic

λmax
232 nm ε=6,000 (based on MW=267)
325 nm ε=7,600 (based on MW=267)

Alkaline

λmax
243 nm ε=7,200
353 nm ε=7,400

Factor A has a characteristic fluorescence pattern. The following fluorescence spectrum of factor A was obtained with an Amino-Bowman Spectrophotofluorometer on an aqueous solution of factor A under acidic, neutral, and alkaline pH.

Acidic

Excitation maximum 327 nm
Emission maximum 398 nm

Neutral

Excitation maximum 324 nm
Emission maximum 396 nm

Alkaline

Excitation maximum 350 nm
Emission maximum 424 nm

The $^{13}$C NMR spectrum of factor A was obtained on a Bruker Model WM 270 NMR Spectrometer. The spectrum showed the following characteristic signals:

$^{13}$C NMR (67.9 MHz, D$_2$O): δ25.66 (1C, t), 26.76 (1C, t), 27.66 (1C, t), 33.19 (1C, t), 63.80 (1C, d), 128.52 (1C, s), 134.72 (1C, d), 135.20 (1C, s), 136.06 (1C, s), 159.86 (1C, s), 174.42 (1C, s), 177.89 (1C, s).

The infrared absorption spectrum of factor A has the following significant absorption peaks:

| IR (KBr) | |
| --- | --- |
| Frequency (cm$^{-1}$) | Intensity[1] |
| 3500-2700 | br, s |
| 2960 | w |
| 2700-2400 | br, m |
| 1719 | s |
| 1660 | shd |
| 1526 | s |
| 1440 | m-w |
| 1410 | m-s |
| 1320 | 2 |
| 1285 | m |
| 1210 | m |
| 1126 | w |
| 1055 | vw |
| 1028 | w |
| 957 | vw |
| 911 | w |
| 878 | vw |
| 836 | vw |

[1]br = broad; m = medium; s = strong; w = weak; vw = very weak; m-s = medium to strong; m-w = medium to weak; shd = shoulder.

The characteristic signals of the NMR spectrum are shown below.

$^1$H NMR (360 MHz, D$_2$O): δ2.30 (1H, m), 2.57 (1H, m), 2.64 (2H, t), 2.74 (1H, dt), 2.81 (1H, dt), 3.05 (1H, dd), 3.15 (1H, ddd), 5.01 (1H, dd), 7.33 (1H, s).

The molecular weight of factor A is 267 as determined by the mass spectral analysis of factor A.

Fast atom bombardment (FAB): m/e 268.
Field desorption: m/e 267, 223.
High resolution FAB: m/e 268.081890; calculated 268.08211 for C$_{12}$H$_{14}$NO$_6$ (M+H$^{30}$).

Elemental analysis carried out on a sample of factor A gave the following percent elemental composition based on the empirical formula of C$_{12}$H$_{13}$NO$_6$.

Calculated: C, 53.93; H, 4.90; N, 5.24; Found: C, 53.72; H, 5.10; N, 5.16.

Factor A has the following specific rotation: $[\alpha]_D^{25}$ (C=1%, H$_2$O) −199.5°.

Electrometric titration carried out on a sample of factor A in 66% dimethylformamide showed the presence of three titratable groups: pK=5.7, 7.5, 12.3.

A-58365 Factor B

The physical and spectroscopic properties of A-58365 factor B are presented in the following paragraphs. As indicated by the following data, factor B appears to be closely related to factor A, differing in structure by one methylene unit.

The infrared absorption spectrum of factor B contains the following significant absorption peaks:

| IR (KBr) | |
| --- | --- |
| Frequency (cm$^{-1}$) | Intensity[1] |
| 3600-2800 | br, s |
| 2960 | m-w |
| 2700-2400 | br, w |
| 1717 | s |
| 1652 | s |
| 1538 | s |
| 1436 | m-w |
| 1412 | s |
| 1350 | vw |
| 1280 | m |
| 1220 | m |
| 1157 | w |
| 1072 | w |
| 1049 | w |
| 1002 | w |
| 906 | w |
| 783 | m-w |
| 639 | br, w |

[1]Abbreviations are as noted hereinabove under factor A IR.

The proton magnetic resonance spectrum ($^1$H NMR) for factor B contains the following signals:

$^1$H NMR (360 MHz, D$_2$O): δ1.67 (1H, m), 1.86 (1H, m), 2.08 (1H, m), 2.35 (1H, m), 2.66 (2H, t), 2.76 (1H, m), 2.78 (2H, m), 2.93 (1H, m), 5.10 (1H, dd), 7.35 (1H, s). The signals at about 1 and about 1.3, and the spike at about 2.05-2.1 are minor impurities.

The carbon nuclear magnetic resonance spectrum of factor B has been run and the following signals are shown in the spectrum.

$^{13}$C NMR (67.9 MHz, D$_2$O): δ16.08 (1C, t), 23.43 (1C, t), 26.07 (1C, t), 26.36 (1C, t), 33.44 (1C, t), 58.03 (1C, d), 126.60 (1C, s), 132.88 (1C, s), 133.06 (1C, d), 137.14 (1C, s), 161.73 (1C, s), 176.97 (1C, s), 178.57 (1C, s).

Factor B absorbs radiation in the ultraviolet region of the spectrum and, like factor A, the maxima observed under neutral and acidic conditions are shifted to longer wave length upon the addition of base. The maxima obtained with an aqueous solution of factor B are as follows:

Neutral and acid: λmax 232 nm (ε=3,800), and λmax 333 nm (ε=5,600). The λmax at 232 nm shifts to 244 nm in base, while the λmax 333 nm shifts to 360 nm in base.

Factor B like factor A fluoresces blue under long wavelength ultraviolet radiation.

The molecular weight of factor B is 281 as determined by mass spectral analysis.

Field desorption mass spectrum: m/e 281 ($M^{30}$).

Based on analysis of the physical and spectral properties of factor B, its empirical formula is $C_{13}H_{15}NO_6$. Comparative analysis of the spectral data of factors A and B indicates that factor B is a higher homolog of factor A.

Factor B has solubility characteristics similar to factor A. Factor B is highly soluble in water and polar organic solvents such as methyl alcohol, ethyl alcohol, dimethylformamide, and dimethylsulfoxide. It is sparingly soluble in acetone and is insoluble in hydrocarbon solvents such as benzene and hexane.

A-58365 Factor C

A further factor produced in less abundance than factors A and B is obtained from the fermentation broth of *S. chromofuscus* NRRL 15098 and is designated as A-58365 factor C. Based on the characteristics of this factor obtained thus far, factor C is similar to both factors A and B. Like the previously described factors, factor C fluoresces blue in long wave length ultraviolet radiation.

The molecular weight of factor C is 295 as determined by mass spectral analysis.

Field desorption mass spectrum: m/e 295 (M+).

Factor C has an empirical formula of $C_{14}H_{17}NO_6$.

The A-58365 factors, although similar, have characteristic retention times on high performance liquid chromatography (HPLC). The individual factors can be separated from one another via HPLC. The HPLC system employed for the separation of the factors utilizes a Waters Associates μ Bondapak C18, 4 nm×300 mm column as the stationary phase. The mobile phase employed consists of 6% acetonitrile/0.3% formic acid/93.7% water at a flow rate of 2.5 ml/min. The characteristic fluorescence of the factors is employed in their detection in the system. The fluorescence is determined on a Schoeffel FS970 spectrophotometer.

The retention times of the factors in the above HPLC system are as follows:

| Factor | Retention (min.) |
| --- | --- |
| A | 4.88 |
| B | 12.47 |
| C | 18.21 |

The structures of the A58365 factors A and B have been determined and are represented by the following structural formulas.

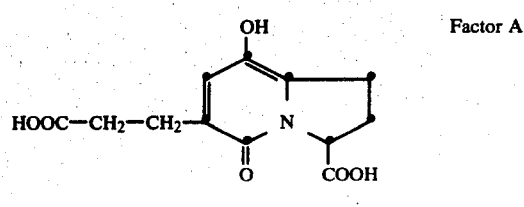

Factor A

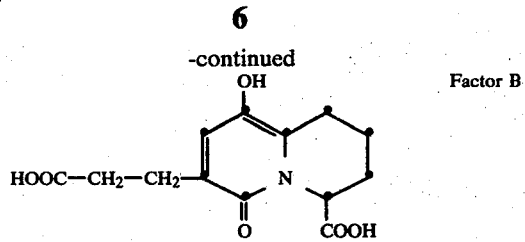

Factor B

The A-58365 factors are acidic compounds possessing two carboxylic acid functional groups. As with most carboxylic acids, the factors described herein are capable of forming salts with suitable bases. Such salts include pharmaceutically acceptable salts useful for the treatment of hypertension as well as salts which are useful in the isolation and purification of the individual factors. Salts formed with the alkali metal and alkaline earth metal bases such as the sodium, potassium, and calcium salts can be formed by neutralizing an aqueous solution of the individual factors with the stoichiometric amount of the base followed by lyophilization of the aqueous salt solution. Suitable bases include, for example, the alkali metal carbonates, bicarbonates and hydroxides such as sodium carbonate, sodium bicarbonate, sodium hydroxide, potassium carbonate, potassium bicarbonate, potassium hydroxide, and calcium hydroxide. Salts of the factors can also be formed with suitable amines such as the primary and secondary amines such as methylamine, ethylamine, isopropylamine, n-butylamine, dimethylamine, cyclohexylamine, dicyclohexylamine, benzylamine, dibenzylamine, abietylamine, procaine, and like basic amines. The ammonium salt of the factors can also be obtained by conventional means. The amine salts can be obtained by adding a solution of the desired amine in a water miscible solvent to an aqueous solution of the factor. Many of the amine salts will precipitate from the aqueous solution or, if soluble in the mixture, can be obtained by lyophilization of the salt solution.

The A-58365 factors inhibit angiotensin I converting enzyme as demonstrated in in vitro studies carried out with isolated guinea pig ileum. The in vitro tests were carried out as follows: segments (2-3 cm long) of the guinea pig ileum were mounted longitudinally in 10 ml isolated tissue baths containing Krebs' solution having the following composition (mmol concentrations): sodium chloride, 118.2; potassium chloride, 4.6; calcium chloride dihydrate, 2.5; monopotassium phosphate, 1.2; magnesium sulfate, 1.2; dextrose, 10.0; and sodium bicarbonate, 24.8. In all experiments tissues were maintained at 37° C. and were aerated with 95% oxygen and 5% carbon dioxide. The ilea were mounted between two electrodes consisting of a stainless steel rod (bottom) and a circular platinum wire (top). Square wave impulses (0.1 Hz) of supramaximal voltage (40 v) and 0.7 msec duration were provided by a Grass S44 stimulator. Tissues were equilibrated for approximately one hour at 1 g of applied force. Isometric responses were recorded on Beckman Dynographs.

Concentration-response curves to 3 or 4 concentrations of angiotensin I were generated. Tissues were then equilibrated with the A-58365 factor ($10^{-6}$ to $10^{-5}$ M) and concentration-response curves to angiotensin I were reassessed. Each tissue was given only one concentration of factor.

In all cases, a significant shift in the contractile response to anigotensin I occurred. The inhibition of ACE in quinea pig ileum was competitive. The data obtained with factors A and B in the abovedescribed test also demonstrated that factors A and B did not inhibit acetylcholine release nor did they block cholinergic receptors. In the in vitro system, A-58365 factors A and B demonstrated pharmacological specificity to inhibit ACE.

The A-58365 factors of this invention are hypotensive agents which, by virtue of their ability to inhibit the enzymatic cleavage of angiotensin I to the pressor agent angiotensin II in mammalian tissue, are useful hypotensive agents. The ability of the ACE inhibiting factors of this invention to lower blood pressure are demonstrated in sodium depleted rats with factor A.

The A-58365 factors are useful in a method for reducing blood pressure in a hypertensive mammal which comprises administering a blood pressure lowering amount of an A-58365 factor of this invention or a pharmaceutically acceptable non-toxic salt thereof. The factors may be administered individually or in any combination, eg. factor A can be administered alone or in combination with factor B. In practicing the method, the A-58365 factor or a pharmaceutically acceptable non-toxic salt thereof is administered orally, intramuscularly, intravenously, or subcutaneously. For parenteral administration the A-58365 factor or a pharmaceutically acceptable salt thereof is dissolved in a physiologically acceptable fluid for injection. Suitable physiological diluents such as Water For Injection, 0.9% saline, 5% glucose or other conventional diluent can be used. For oral administration the A58365 factor or a pharmaceutically acceptable non-toxic salt thereof may be formulated as capsules, tablets or liquid suspensions. The A-58365 factor or a pharmaceutically acceptable salt thereof can be administered in a non-toxic single daily dose of between about 100 mg/kg and about 2,000 mg/kg of body weight. Alternatively, it can be administered in multiple daily doses. The precise regimen will depend on such factors as the level of hypertension in the patient and the drug tolerance for the individual as well as other factors.

The ACE inhibitory factors are prepared by culturing *Streptomyces chromofuscus NRRL* 15098 under aerobic fermentation conditions in an aqueous nutrient culture medium containing assimilable sources of carbon, inorganic salts and nitrogen. The culture medium employed in the fermentation can be any one of a number of media since the microorganism is capable of utilizing energy from a variety of nutrient sources. For example, a variety of carbohydrates including sugars and starches can be included in the culture medium to supply the carbon requirements of the microorganism. Likewise, various sources of nitrogen such as the amino acids, distillers extracts, meat peptones, and casein hydrolysates can be employed in the culture medium. In the interest of economy in production, optimal yield, and ease of isolation of the ACE factors, certain culture media are preferred. For example, one of the preferred sources of carbon is potato dextrin, although various sugars such as glucose or fructose may also be used. Preferred sources of nitrogen are peptones and the hydrolysates of casein. As is common in the fermentation of microorganism, nutrient inorganic salts can be incorporated in the culture medium for the production of the ACE factors. Such inorganic salts are the customary salts capable of yielding sodium, potassium, ammonium, calcium, phosphate, chloride, carbonate, and like ions. Trace elements may also be added to the fermentation medium; however, these are commonly added in sufficient trace amounts as constituents of other ingredients added to the media.

During the fermentation of *S. chromofuscus* NRRL 15098 to produce the A-58365 factors, cobaltous ion or other divalent cation is added to the fermentation medium. Cobaltous chloride is a convenient source of divalent cobalt. The divalent cation such as cobaltous ion is added in minor amounts, for example, the addition of between about 5 mg and about 15 mg of cobaltous chloride hexahydrate per liter of medium is sufficient.

The fermentation can be carried out at temperatures between about 23° C. and about 30° C. However, best yields are obtained when the fermentation is carried out at 25° C. During the fermentation the pH of the medium increases. Generally, the initial pH of the broth is adjusted to about 7, and the terminal pH is about 8 to 8.3.

The fermentation is carried out under aerobic conditions. Sterile air is passed through the fermentation medium with stirring during the course of the fermentation. For best results, the dissolved oxygen level in the fermentation medium should be maintained at approximately 30 to 40% of air saturation.

An antifoam agent is generally beneficial to prevent excess foaming and any of the commonly employed antifoam agents such as the silicone antifoam agents can be employed in the fermentation.

The production of the ACE inhibitory factors during the course of the fermentation is followed by high performance liquid chromatography assay of an aliquot of the broth withdrawn from time to time. Peak production generally occurs between about 70 and about 90 hours into the fermentation. The assay is carried out employing as the stationary phase a 4 mm $\times$ 300 mm$\mu$ Bondapak C18 column (Waters Associates), and a mobile phase comprising acetonitrile:formic acid:water (6:0.3:93.7, v:v:v). The flow rate is 2.5 ml/min. Detection of the factors is carried out with a Schoeffel model FS970 spectrofluorometer by employing the wave length $\lambda exc = 327$ nm, and a 370 nm emission cut off filter.

In carrying out the fermentation, a small volume of vegetative medium is inoculated with a lyophilized pellet of *S. chromofuscus* NRRL 15098. Incubation of the culture is carried out at about 30° C. and, following the attainment of good growth which generally occurs in about two days, the vegetative medium or portions thereof are employed to inoculate a larger scale medium known as a "bump" medium. The "bump" medium is an intermediate-size medium used as a large inoculum for large scale fermentation tanks. In general, the "bump" medium has the same or approximately the same composition as the vegetative medium. The initial small-volume vegetative medium can be a highly nutritive medium used for culturing microorganisms. A suitable vegetative medium which provides good growth of *S. chromofuscus* NRRL 15098 is composed of trypticase soy broth plus approximately 1% glucose. Trypticase soy broth is a commercially available soybean-casein digest containing pancreatic digest of casein, soy peptone (a digest of soybeans), sodium chloride, dipotassium phosphate and glucose.

Alternatively, the lyophilized pellet of *S. chromofuscus* can be initially grown on an agar slant and, following growth, spores on the agar slant are transferred under sterile conditions to a vegetative medium. The grown vegetative medium can then be employed as described above for the inoculation of intermediate size "bump" media.

The microorganism employed in the method for producing the ACE inhibitors of this invention has been identified as a new strain of *Streptomyces chromofuscus* (Preobrashenskaya, Blinov and Ryabova 1957), Pridham, Hessetine and Benedict, "A guide for the Classification of Streptomycetes According to Selected Groups", *Appl. Microbiol.* 6:52–59, (1957).

The new strain of *S. chromofuscus* has been deposited without restriction as to public availability in the permanent collection of the Agricultural Research Culture Collection, Northern Regional Research Center, Department of Agriculture, 1815 North University Street, Peoria, IL 61604, where it has been assigned the accession number NRRL 15098.

The parent culture from which the new strain was selected was isolated from a soil sample collected in Brazil, South America.

The following paragraphs and tables contain the taxonomic description of the new strain as determined by standard methods and also comparisons with published taxonomic descriptions of Streptomyces resembling the new strain.

The methods recommended by the International Streptomyces Project (ISP) for the characterization of Streptomyces species have been followed along with certain supplementary tests, Shirling, E. B. and Gottlieb, D., 1966, "Methods of Characterization of Streptomyces Species," *Int. J. Syst. Bacteriol.* 16 (3), pp. 313–340.

Cultural Characteristics of *S. chromofuscus* NRRL 15098

Table 1 below contains the description of growth of the new strain on various culture media. The color names in the Table were assigned by reference to the ISCC-NBS Centroid Color Charts, standard sample No. 2106, U.S. Department of Commerce, National Bureau of Standards, 1958; and Tresner, H. D. and Backus, E. J., 1956, "System of Color Wheels for Streptomycete Taxonomy", *Appl. Microbiol.*, 11, 335–338; and to the *Color Harmony Manual*, 4th edition, Color Standards Department, Container Corporation of America, Illinois, 1958. In summary, *S. chromofuscus* NRRL 15098 produces an abundant serial mycelia having a spore mass color in the gray (GY) color series. The nearest matching color tab for the gray color series in the Tresner and Backus system is 2 dc yellowish gray to 2 fe medium gray. In the ISCC-NBS system, the nearest matching color chip is 112, light olive gray and 93, yellowish gray. This cultural feature is produced on yeast-malt extract agar (ISP No. 2), oatmeal agar (ISP No. 3), glycerolasparagine agar (ISP No. 5), Czapek's solution agar and tomato paste oatmeal agar. This growth and color feature is best observed when grown on inorganic salts-starch agar (ISP No. 4). The color of the reverse side is yellow-brown. This reverse color is unaffected by pH. No soluble pigment is produced in any media except ISP No. 5, where a light yellow pigment is present.

TABLE 1

| Cultural Characteristics of *S. chromofuscus* NRRL 15098 | |
|---|---|
| Medium | Growth Characteristic[1] |
| ISP No. 2[2] | Abundant growth; abundant aerial mycelia: 2dc Yellowish Gray (GY); reverse: 69; deep OY; no soluble pigment. |
| ISP No. 3 | Fair growth; reverse: 91.d.gy.Y; poor aerial mycelial growth: 5fe Light Grayish |
| ISP No. 4 | Reddish; no soluble pigment. Abundant growth; reverse: 5b. deep Br; abundant aerial mycelia: 2fe Medium Gray (GY); no soluble pigment. |
| ISP No. 5 | Fair growth; reverse: 94.1.01 Br; Fair aerial mycelial development: 2dc Yellowish Gray (GY); Light Yellow soluble pigment. |
| Czapek's Agar | Fair growth; reverse: 79.1.gy.yBr; Fair aerial mycelial development: 3ge Light Grayish Yellowish Brown (GY); no soluble pigment. |
| TPO[3] | Abundant growth; reverse: 75. deep yBr; abundant aerial mycelia: 3ge Light Grayish Yellow Brown (GY); no soluble pigment. |

[1]The numbers and letters used for reverse side colors refer to the color charts of ISCC-NBS Centroid Color Charts Standard Sample No. 2106, U.S. Department of Commerce, National Bureau of Standards. The underlined numbers and letters used to designate color of the aerial mycelia refer to Tresner, H. D. and Backus, E. J. 1956, "System of Color Wheels for Streptomycete Taxonomy", Appl. Microbiol. 11:335–338.,(GY) refers to the Gray series.
[2]ISP = International Streptomyces Project Media
[3]TPO = Tomato paste oatmeal agar Morphological Characteristics of *S. chromofuscus* NRRL 15098

The new strain of *S. chromofuscus* produces well-developed, non-fragmented mycelia which are monopodially branched. Sporophores are produced on aerial hyphae forming spirals of 4–5 coils. Some spirals form very tight balls at the end of the sporophore. These balls could be mistaken for sclerotio. Spores are oblong with a spiny surface. The new strain is placed in the Spirales (S) section of Pridham, et al., Pridham, T. G., Hesseltine, C. W., and Benedict, R. G., 1957, "A Guide for the Classification of Streptomycetes According to Selected Groups", *Appl. Microbiol.* 6:52–79.

Morphology was studied with an optical light microscope. A scanning electron microscope (SEM) was used to study the spore surface and ornamentation.

Physiological Characteristics of *S. chromofuscus* NRRL 15098

Analysis of hydrolyzed whole cells of the *S. chromofuscus* strain indicated the presence of LL-diaminopimelic acid. No meso isomer was detected. Sugar analysis of hydrolyzed whole cells showed the presence of glucose, mannose, ribose, and rhamnose. These results show that the cell wall of the strain is a Type I cell wall with no characteristic sugar pattern and is indicative of the genus Streptomyces, Buchanan, R. E. and Gibbons, N. E. (eds.) 1974, *Bergey's Manual of Determinative Bacteriology*, 8th edition, The Williams and Wilkins Co., Baltimore, MD.

The carbon utilization pattern for *S. chromofuscus* NRRL 15098 is shown in the following Table 2. Carbon utilization was determined with ISP basal medium to which sterilized carbon sources were added to equal a final concentration of 1.0 percent. Plates were incubated at 30° C. and were read after 14 days.

TABLE 2

Carbon Utilization of *S. chromofuscus* NRRL 15098

| Carbon Source | Utilization[1] |
|---|---|
| No Carbon | − |
| L-arabinose | + |
| D-fructose | + |
| D-glucose | + |
| i-inositol | + |
| D-mannitol | + |
| raffinose | − |
| L-rhamnose | + |
| sucrose | ± |
| D-xylose | + |
| D-arabinose | + |
| cellobiose | + |
| D-galactose | + |
| lactose | + |
| D-maltose | + |
| melbiose | + |
| sodium acetate | − |
| sodium citrate | + |
| sodium succinate | + |
| D-ribose | + |
| salicin | + |

[1] − = no utilization
+ = utilization
± = doubtful utilization

*S. chromofuscus* NRRL 15098 will hydrolyze starch and partially hydrolyze skim milk. A dark-brown growth ring is formed on skim milk. Gelatin is not hydrolyzed by the new strain. In ISP No. 8, organic nitrate broth, the strain fails to reduce nitrates to nitrites.

The new strain will tolerate up to about 7 percent sodium chloride.

The new strain will grow at temperatures between about 15° C. and about 40° C.

TABLE 3

Melanoid Pigment Formation of *S. chromofuscus* NRRL 15098

| Medium | Pigment Formation |
|---|---|
| ISP No. 1 tryptone-yeast extract broth | + |
| ISP No. 6 peptone-yeast extract iron agar slant | + |
| ISP No. 7 tyrosine agar | + |
| ISP No. 7 agar slants without tyrosine | − |

Based upon comparisons of the morphological, cultural, and physiological characteristics of the A-58365-producing organism with the published descriptions of similar species, the culture described herein was most similar to *S. chromofuscus*, Shirling, E. B. and Gottlieb, D., 1968, "Cooperative Description of Type Cultures of Streptomyces", *Int. J. Syst. Bacteriol.* 18 (4): 279–392. However, the A-58365 organism differs from the published species and is therefore classified as a new strain thereof. Although having many similar characteristics, the known *S. chromofuscus* strain differs from the A-58365 strain provided herein by not utilizing the sugar raffinose and by the lack of melanoid pigment production on ISP No. 7 agar.

*S. chromofuscus* NRRL 15098, in addition to producing the ACE inhibitors described herein, also produces in minor amounts the antibiotic asukamycin, AM1042 and another antibiotic metabolite which may be methylenomycin. Asukamycin is described by Omura, et al., U.S. Pat. No. 4,226,879, October 7, 1980, and is produced by *Streptomyces nodosus* NRRL 8185. *S. nodosus* differs culturally from *S. chromofuscus* NRRL 15098 in its distinctive reverse and soluble pigmentation. Morphological differences are: poor sporophore development, short sport chain, and smooth spore surface ornamentation. Physiologically *S. nodosus* differs from the new strain herein in not producing melanoid pigments in ISP No. 1 broth or on ISP No. 6 and ISP No. 7 agar slants. These differences show that *S. nodosus* is a separate and distinct species from the organism described herein.

The other antibiotic metabolite produced during the growth of *S. chromofuscus* NRRL 15098 has been tentatively identified as methylenomycin. This antibiotic, previously reported to be produced by *Streptomyces violaceoruber* 2416, is described by Haneishi, T., et al., *J. Antibiotics*, 27, 386–392 (1974).

The A-58365 factors A and B are isolated from the fermentation medium and are separated from one another by chromatography. The isolation and separation of the factors is carried out as follows. The whole fermentation broth is acidified to about pH 2.0 and is filtered to remove the mycelium and other insolubles. A filter aid is desirably used and enhances the rate of filtration. Following the filtration the pH of the filtered broth is adjusted to about pH 7.0 with a base such as sodium hydroxide. In a preliminary chromatography to remove inactive neutral impurities, the neutral filtered broth is treated with a nonfunctional polymeric reticular resin, for example, a polystyrene resin such as Diaion HP-20 (Mitsubishi Chemical Co.) or a XAD resin (Rohm and Haas, Philadelphia PA). The neutral broth may be passed through a column packed with the resin or, alternatively, the resin may be added to the neutral broth in a suitable vessel and stirred with the broth to adsorb the inactive impurities. In this preliminary purification of the broth the resin is used in an amount corresponding to about one-tenth of the volume of the broth. Preferably, the resin is stirred in the neutral broth for about two hours and is then separated by filtration. The pH of the resin-treated broth is then lowered to about pH 2.0–3.0 with an acid such as hydrochloric acid and the acidified broth is chilled and filtered to remove an inactive precipitate.

The acidic, polished broth is next chromatographed over a nonfunctional resin, preferably Diaion HP-20. The acidic broth is poured onto a column packed with the HP-20 resin and the effluent discarded. After the column is washed with a dilute acid, preferably 0.3% aqueous formic acid, the A-58365 factors are eluted by gradient elution employing a gradient from water:formic acid (99.7:0.3, % by vol.) to acetonitrile:water:formic acid (20:79.7:0.3, % by vol.). Multiple fractions are collected with factor A eluting in the early active fractions and factors B and C eluting in the later active fractions. The course of the chromatography is followed by the HPLC assay described herein.

The A-58365 factor A containing factors are pooled and concentrated by evaporation. The concentrate is then applied to an acidic resin such as a polystyrene sulfonic acid resin in the acid cycle, for example, Dowex 50W resin (Dow Chemical Co.). Factor A is washed from the resin with deionized water in multiple fractions. The factor A containing fractions are combined and concentrated by evaporation.

The acidic (pH 2–3) concentrate of factor A is filtered and then subjected to reverse phase preparative HPLC on $C_{18}$ silica gel such as octadecylsilanized Whatman LP-1 or Water's Asoc. $C_{18}$ silica gel. The column is developed first with aqueous formic acid (0.3:99.7% by vol.), next with acetonitrile:formic acid:water (1.0:0.3:98.7% by vol.), and finally with acetonitrile:formic acid:water (2.5:0.3;97.2% by vol.). The fractions containing factor A are pooled and concentrated by evaporation.

The factor A concentrate from the HPLC column is then chromatographed over an anion exchange resin such as 100–200 mesh BioRex 5 resin in the chloride cycle (BioRad Laboratories, Richmond, CA). The column is eluted with about 0.2 M to about 0.5 M sodium chloride and pure factor A containing fractions are combined. The pooled fractions are acidified to about pH 2.2–2.5 with acid, eg. 1 N hydrochloric acid, and are passed over Diaion HP-20 resin to remove salts present in the fractions from the anion exchange chromatography. Prior to use, the HP-20 resin is prepared with 0.01 N hydrochloric acid. Factor A is eluted by first washing the column with dilute acid (pH 2.3), next with water and finally with aqueous acetonitrile (15:85% by volume). The factor A containing fractions are pooled, concentrated by evaporation, and the concentrate is lyophilized to provide pure factor A as an amorphous white powder.

The combined fractions containing factors B and C, obtained as described above by gradient elution from the HP-20 chromatography of polished broth, are concentrated to a smaller volume by evaporation. The concentrate of factors B or C is next chromatographed over a polystyrene polysulfonic acid resin such as Dowex 50W (H+) (Dow Chemical Co.). Factors B or C are washed from the resin with deionized water. The fractions containing factor B are combined and concentrated. Factor C containing fractions are likewise combined and concentrated.

The concentrates of factors B and C are separately purified by reversed phase HPLC using $C_{18}$ silica gel eg., octadecylsilanized Whatman LP-1 silica gel. Factor B is eluted from its chromatogram using first formic acid:water (0.3:99.7% by vol.), next acetonitrile:formic acid:water (6.0:0.3:93.7%), and finally acetonitrile:formic acid:water (15.0:0.3:84.7% by vol.). Factor C may be eluted from its chromatogram using similar solvent systems containing, however, a higher concentration of acetonitrile in the solvent mixture. The active fractions off the chromatograms are combined and concentrated.

The concentrates of factors B and C can be further purified by following the procedures described above for factor A. For example each concentrate is chromatographed over an anion exchange resin, the respective eluents acidified, desalted over a nonfunctional resin, and the desalted eluents lyophilized.

Factor A is produced in greater abundance than factors B and C and is the preferred ACE inhibitor of this invention. Factor B in turn is produced in greater amounts than is Factor C.

As is mentioned hereinafter, the antibiotic asukamycin and another antibiotic metabolite (possibly methylenomycin) are produced in minor amounts along with the ACE inhibitory factors. During the isolation and purification of the A-58365 factors as described above, the antibiotic metabolites are lost.

The following Examples further illustrate the present invention.

EXAMPLE 1

Production and Isolation of A-58365 Factors

A lyophilized pellet of *S. chromofuscus* NRRL 15098 was used to inoculate 50 ml of a sterilized vegetative medium of three percent trypticase soy broth containing one percent glucose. The inoculated medium was incubated at 30° C. for 48 hours with shaking. This vegetative medium was used to inoculate bump media as follows. Two, 2,000 ml flasks each containing 400 ml of three percent trypticase soy broth with one percent glucose added were each inoculated with 10 ml of the vegetative medium. The bump cultures were then incubated for 24 hours at a temperature of 30° C.

Both of the bump cultures were used to inoculate 100 liters of production medium. The production medium had the following composition.

| Ingredient | Concentration (g/l) |
| --- | --- |
| Dow-Corning antifoam A | 0.2 |
| Potato Dextrin | 35 |
| Yeast | 0.25 |
| OM Peptone[1] | 20 |
| $COCl_2.6H_2O$ | 0.01 |
| L-Proline | 4 |
| N-Z Amine A[2] | 4 |
| Deionized water | qs. to 100 l. |

[1]OM Peptone is a soluble meat peptone, Amber Laboratories, Juneau, WI
[2]N-Z Amine A is an enzymatic hydrolysate of casein, Humko Sheffield Chemical, Lyndhurst, NJ.

The pH of the medium was adjusted to 7.0 with 5 N sodium hydroxide before sterilization. After sterilization the medium was inoculated with the bump media described above and the production fermentation was allowed to proceed at a temperature of 25° C. for 90 hours. During the fermentation sterile air was passed through the medium, with stirring, at a rate sufficient to maintain the dissolved oxygen content of the medium at about 30% to about 40% of air saturation.

The pH of the medium increased during the fermentation to a terminal pH of 8.3.

During the fermentation the medium was assayed for A-58365 factor content by employing the HPLC system described hereinabove. The factors were detected by fluorescence using a Schoeffel Model FS970 spectrophotofluorometer at the wave length $\lambda exc.=327$ nm with a 370 nm cutoff filter. The production medium assayed for about 11.5 mcg/ml after the 90 hour fermentation period.

Three, 100-liter fermentations carried out as described above were separately acidified in the fermentors to pH 2.0 with concentrated hydrochloric acid. The acidified whole broths were combined and filtered with the aid of 2% Hyflo filter aid. The pH of the filtered broth was adjusted to 7.0 with 5 N sodium hydroxide. The nonfunctional resin Diaion HP-20 was added to the neutral broth in an amount corresponding to one-tenth the volume of the filtered broth and the resin-broth mixture was stirred for two hours. The broth was separated from the resin and acidified to pH 2.0 with 5 N hydrochloric acid. The acidified broth was chilled and filtered to remove inactive precipitates. The acidified broth was applied to a 20'×4" i.d. column containing 20 l. of Diaion HP20 and the effluent discarded. The column was next washed with 60 l. of 0.3% aqueous formic acid and the effluent discarded. The A-58365 factors were then eluted with a 100 l. gradient from water-formic acid (99.7:0.3; v:v:v:) to acetonitrile-water-formic acid (20:79.7:0.3; v:v:v.) and 2 l. fractions were collected. Fractions 27 to 48 containing factor A were pooled and concentrated in vacuo to a volume of 750 ml. Elution was continued with 20 liters of acetonitrile-water-formic acid (20:79.7:0.3). Fractions 56 to 63 containing factor B were pooled and concentrated to a volume of 350 ml.

The factor A containing concentrate was applied to a 9.3 cm×80 cm (5 l.) column of Dowex 50W×2 ($H^+$) and the column was eluted with about 17 l. of deionized water. One-liter fractions from 9 to 15 liters of eluted volume containing factor A were collected, pooled and concentrated to about 200 ml.

The factor A concentrate (pH 2-3) was filtered and chromatographed on reverse phase HPLC on a 8 cm×1 m column (Jobin Yvon Chromatospac Prep instrument) containing approximately 2.5 kg (4-4.5 l.) of octadecyl-silanized Whatman LP-1 silica gel. The column was developed first with two liters of formic acid-water (0.3:99.7, v:v), then with 5 liters of acetonitrile-formic acid-water (1.0:0.3:98.7, v:v:v), and, finally with 20 l. of acetonitrile-formic acid-water (2.5:0.3:97.2, v:v:v). Fractions of 500 ml volume were collected. Fractions 32-44 containing factor A were pooled and concentrated by evaporation to a volume of 200 ml.

The factor A concentrate from HPLC was applied to 2.5 cm×30 cm (180 ml) column of 100-200 mesh BioRex 5 ($Cl^-$) resin (BioRad Laboratories, Richmond, CA). The resin was washed with deionized water and both the wash and effluent were discarded. The column was developed with 400 ml of 0.20 M sodium chloride and then with 2200 ml of 0.35 M sodium chloride. Fractions of 20 ml in volume were collected and fractions 106-140 containing pure factor A were pooled. The pH of the pooled fractions were adjusted to 2.3 with 1 N hydrochloric acid and the acidified pool was applied to a 2.8 cm×19 cm (120 ml) column of Diaion HP20 set in 0.01 N hydrochloric acid. The column was washed first with 100 ml of deionized water acidified to pH 2.3 with dilute hydrochloric acid, then with 220 ml of deionized water (pH 5.9), and was then eluted with 340 ml of acetonitrile-water (15:85, v:v). After multiple fractions totaling about 180 ml in volume had been collected, the fractions from 0-180 ml of effluate were collected, combined, concentrated by evaporation and lyophilized to give 1.31 g of pure factor A.

The concentrate of pooled factor B containing fractions, eluted from the Diaion HP-20 column as described above, was applied to a 9.3 cm×80 cm (5 l.) column of Dowex 50W×2 ($H^+$ cycle) resin. The column was eluted with 32 l. of deionized water and factor B was collected in one liter fractions from 10 to 14 liters of eluate. The active fractions were combined and concentrated to a volume of about 250 ml.

The A-58365 factor B containing concentrate was then subjected to the same reverse phase HPLC as described above for the purification of factor A. The column was developed first with two liters of formic acid-water (0.3:99.7 % by vol.), next with acetonitrile-formic acid-water (6.0:0.3:93.7 % by vol.) and then with acetonitrile-formic acid-water (15.0:0.3:84.7, % by vol.). Multiple fractions of about 500 ml. were collected. Fraction 24 containing factor B was concentrated by evaporation to a volume of 100 ml.

The concentrate of factor B was further purified on an anion exchange resin as follows. A 2.0 cm i.d.×25 cm column packed with BioRex 5 ($Cl^-$) anion exchange resin was charged with the concentrate and the column was eluted first with 200 ml of 0.2 M sodium chloride followed by elution with 1600 ml of 0.35 M sodium chloride. Multiple fractions of 10 ml volume were collected and fractions 193-210 were pooled. The pH of the pooled fractions was adjusted to pH 2.3 with 1 N hydrochloric acid and the acidified pool was applied to an 8 mm i.d.×20 cm (10 ml) Diaion HP-20 column set in 0.01 N hydrochloric acid. The column was washed first with 300 ml of deionized water (adjusted to pH 2.3) then with 14 ml of deionized water (pH 5.9). The effluent and wash were discarded and factor B was eluted with 44 ml of acetonitrile-water, (15:85 % by vol.). Multiple fractions of 2 ml volume were collected. Fractions 8 to 11 were pooled and concentrated to a volume of 1 ml. The concentrate was lyophilized to give 2.9 mg of pure factor B.

EXAMPLE 2

Production of A-58365 Factors A and B With Proline and Lysine Supplemented Culture Medium

*S. chromofuscus* NRRL 15098 was cultured in vegetative medium prepared and cultured as described by Example 1 and the culture medium was used to inoculate a production medium having the following composition.

| Ingredient | Concentration (g/l) |
| --- | --- |
| Potato Dextrin | 25 |
| NZ Amine A[1] | 3 |
| Yeast | 0.25 |
| L-Proline | 3 |
| Beef Extract | 1 |
| CO $Cl_2.6H_2O$ | .01 |
| L-Lysine | 2 |
| Deionized water | qs 1000 ml |

[1]Enzymatic hydrolysate of casein, Humko Sheffield Chemical, Lyndhurst, NJ.

The pH of the medium was adjusted to 7.0 with 5 N sodium hydroxide prior to sterilization. After sterilization the medium was inoculated and cultured at a temperature of 30° C. for 96 hours.

The fermentation medium was assayed for factor content during the fermentation by employing the HPLC system described hereinabove.

Factor B is recovered from the filtered fermentation broth, isolated, and purified by the chromatographic procedures described by Example 1.

I claim:

1. In the process for producing angiotensin I converting enzyme inhibitor A-58365 factor B, which comprises cultivating *Streptomyces chromofuscus* NRRL 15098 in an aqueous nutrient culture medium containing assimilable sources of carbon, nitrogen, and inorganic salts under aerobic fermentation conditions, the improvement which comprises supplementing said culture medium with between about 1 g and about 6 g of proline per liter of said culture medium and with between about 1 g and about 3 g of lysine per liter of said culture medium.

2. The process of claim 1 comprising the further step of isolating A-58365 factor B.

3. The process of claim 1 wherein said culture medium is supplemented with between about 3 g and about 4 g of proline per liter of said culture medium and with about 2 g of lysine per liter of said culture medium.

4. The process of claim 1 or 3 wherein the culture medium is supplemented with L-proline and L-lysine.

* * * * *